(12) United States Patent
Kim et al.

(10) Patent No.: US 10,330,577 B2
(45) Date of Patent: Jun. 25, 2019

(54) METHOD FOR MEASURING DENSITY CHANGE OF UNDERGROUND MATERIAL USING GRAVIMETER

(71) Applicant: KOREA INSTITUTE OF GEOSCIENCE AND MINERAL RESOURCES (KIGAM), Daejeon (KR)

(72) Inventors: Jeong Woo Kim, Calgary (CA); Neumeyer Juergen, Calgary (CA)

(73) Assignee: KOREA INSTITUTE OF GEOSCIENCE AND MINERAL RESOURCES (KIGAM), Daejeon (KR)

( * ) Notice: Subject to any disclaimer, the term of this patent is extended or adjusted under 35 U.S.C. 154(b) by 257 days.

(21) Appl. No.: 15/301,057

(22) PCT Filed: Mar. 2, 2015

(86) PCT No.: PCT/KR2015/001973
§ 371 (c)(1),
(2) Date: Sep. 30, 2016

(87) PCT Pub. No.: WO2015/152521
PCT Pub. Date: Oct. 8, 2015

(65) Prior Publication Data
US 2017/0038286 A1 Feb. 9, 2017

(30) Foreign Application Priority Data

Apr. 3, 2014 (KR) .................. 10-2014-0040028

(51) Int. Cl.
*G01N 9/36* (2006.01)
*E21B 49/08* (2006.01)
(Continued)

(52) U.S. Cl.
CPC .......... *G01N 9/36* (2013.01); *E21B 41/0064* (2013.01); *E21B 47/10* (2013.01); *E21B 49/08* (2013.01);
(Continued)

(58) Field of Classification Search
USPC ........................................... 73/30.04
See application file for complete search history.

(56) References Cited

U.S. PATENT DOCUMENTS 3,747,403 A * 7/1973 Yungul ................. G01V 7/00
73/152.02
5,204,568 A * 4/1993 Kleinberg ........... F16C 32/0438
310/90.5
(Continued)

*Primary Examiner* — Daniel S Larkin
(74) *Attorney, Agent, or Firm* — Norton Rose Fulbright US LLP

(57) ABSTRACT

Provided is a method of measuring a change in the density of an underground material. To measure the change in the density of the underground material, a borehole is installed above a target underground material and a first gravimeter and a second gravimeter are installed outside and inside of the borehole, respectively. Sequentially, a change in the density of the target underground material is calculated based on a first gravitational change and a second gravitational change measured using the first gravimeter and the second gravimeter. According to the method, it is possible to precisely measure the change in the density of the target underground material, such as an oil, a gas, etc., stored in an underground reservoir and carbon dioxide injected into an underground storage.

9 Claims, 2 Drawing Sheets

(51) Int. Cl.
   *G01V 7/00*    (2006.01)
   *G01N 9/00*    (2006.01)
   *E21B 41/00*   (2006.01)
   *E21B 47/10*   (2012.01)

(52) U.S. Cl.
   CPC .............. *G01N 9/00* (2013.01); *G01V 7/00* (2013.01); *E21B 2049/085* (2013.01); *Y02C 10/14* (2013.01)

(56) References Cited

U.S. PATENT DOCUMENTS

| | | | |
|---|---|---|---|
| 5,448,912 A * | 9/1995 | Black .................... | G01V 7/16 73/152.02 |
| 2013/0283888 A1* | 10/2013 | DiFoggio ............... | G01N 9/36 73/30.04 |
| 2014/0083186 A1* | 3/2014 | Levitt .................... | G01V 7/00 73/382 R |

* cited by examiner

METHOD FOR MEASURING DENSITY CHANGE OF UNDERGROUND MATERIAL USING GRAVIMETER

CROSS-REFERENCE TO RELATED APPLICATION

This application is a national phase application under 35 U.S.C. § 371 of International Application No. PCT/KR2015/001973 filed on Mar. 2, 2015, which claims priority to and the benefit of Korean Patent Application No. 2014-0040028, filed on Apr. 3, 2014. The disclosures of the referenced applications are incorporated into the present application by reference in their entireties.

BACKGROUND

1. Field of the Invention

The present invention relates to a method of measuring a change in the density of an underground material using a gravimeter, which is possible to sequentially measure a change in distribution and leakage of an oil or a gas stored in a reservoir or carbon dioxide stored in an underground storage.

2. Discussion of Related Art

Recently, due to environmental problems such as global warming, etc., the capture of carbon dioxide and ocean, underground, and surface storage of the captured carbon dioxide have been largely researched. In methods of storing captured carbon dioxide, the ocean storage may cause the destruction of a marine ecosystem, the surface storage is still in the early stage technology due to a repository of mineral formed of fixed carbon dioxide, and the underground storage is acknowledged as a most representative storage method among them.

After the underground storage of carbon dioxide, it is necessary to regularly monitor it. While moving upward through cracks in faults or rocks, stored carbon dioxide pollutes groundwater or leaks into the air or seawater so as to affect an ecosystem. The Norwegian Energy Company performed seismic profiling after injecting 2,300,000 tons of carbon dioxide in 1999 and 4,400,000 tons of carbon dioxide in 2001 into the ground and compared the result of the seismic profiling with data in 1994 in which carbon dioxide was not injected, thereby verifying the existence of the movement of carbon dioxide after injecting the carbon dioxide.

To allow the underground storage of carbon dioxide to be invigorated, development in technology for monitoring the movement of carbon dioxide stored in the ground is required.

Also, to efficiently use fossil fuel which is being exhausted, technologies for monitoring the movement of an oil or a gas stored in a reservoir are required. Using the technologies, since it is possible to observe reserves and a change in distribution of an oil or a gas stored in a reservoir in real time during a mining process, it is very helpful to set up an underground resource mining project.

SUMMARY OF THE INVENTION

The present invention provides a method of precisely measuring a change in the density of a target underground material by vertically coupling a gravimeter installed on the surface of the earth with a gravimeter installed in a borehole.

According to an aspect of the present invention, there is provided a method of measuring a change in the density of an underground material. The method includes forming a borehole above a target underground material, installing a first gravimeter and a second gravimeter outside and inside of the borehole, respectively, measuring a first gravitational change and a second gravitational change using the first gravimeter and the second gravimeter, respectively, and calculating a change in the density of the target underground material based on the first gravitational change and the second gravitational change. The target underground material may be one selected from the group consisting of an underground oil, a gas, and carbon dioxide. Information about an earth crust material existing above the target underground material may be obtained in the forming of the borehole, and the second gravimeter may be installed at a position set based on the information about the earth crust material. The information about the earth crust material may include information on a content and distribution of an underground fluid, which varies with a depth of the borehole, and the second gravimeter may be installed at a position at which a difference between an absolute value of a first gravitational force of the underground fluid acting on the first gravimeter and an absolute value of a second gravitational force of the underground fluid acting on the second gravimeter is present within a preset error tolerance range. The error tolerance range may be from about −10 μGal to about +10 μGal.

The change in the density of the target underground material may be calculated using a sum of the first gravitational change and the second gravitational change.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
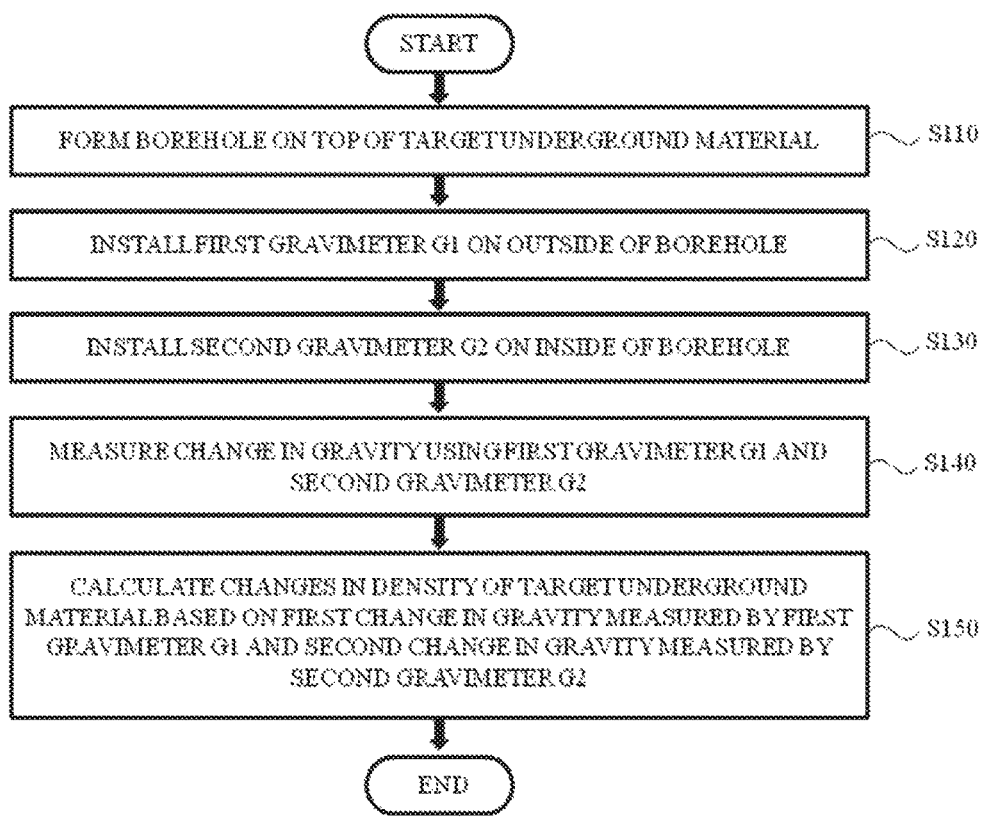
FIG. 1 is a flowchart illustrating a method of measuring a change in the density of an underground material according to an exemplary embodiment of the present invention.

Hereinafter, embodiments of the present invention will be described in detail with reference to the attached drawings. Since embodiments of the present invention may have various modifications and several shapes, an exemplary embodiment will be shown in the drawings and will be described in detail. However, it is not to limit the present invention to the exemplary embodiment but should be understood as including all modifications, equivalents, and substitutes included in the thought and scope of the present invention. While describing the respective drawings, like reference numerals designate like elements. In the attached drawings, sizes of structures are more enlarged than they actually are for clarity of the present invention.

Terms are used herein only to describe the exemplary embodiment but not to limit the present invention. Singular expressions, unless defined otherwise in contexts, include plural expressions. It will be further understood that the terms "comprises" and/or "comprising" used herein specify the presence of stated features or components, but do not preclude the presence or addition of one or more other features or components.

All terms including technical or scientific terms, unless defined otherwise, have the same meaning generally understood by a person of ordinary skill in the art. It will be understood that terms defined in dictionaries generally used are interpreted as including meanings identical to contextual meanings of the related art, unless definitely defined otherwise in the present application, and are not interpreted as including ideal or excessively formal meanings.

When a change in gravity is measured using a gravimeter at a ground level above a target underground material which may move below the ground level, such as an oil, a gas, etc., stored in an underground reservoir and carbon dioxide injected into an underground storage, a measured gravity value may vary with the movement of the target underground material. However, when the change in gravity is measured using the gravimeter at the ground level above the target underground material as described above, the change in gravity measured by the gravimeter is influenced not only by the movement of the target underground material but also by earth tide, ocean loading, polar motion, a change in atmospheric pressure, and the movement of soil moisture and ground water in the ground.

The influences of the earth tide, ocean loading, and polar motion, and change in atmospheric pressure may be relatively calculated more appropriately due to various models and actual measurement. Accordingly, the influences thereof may be easily removed from the change in gravity measured by the gravimeter.

However, it is not easy to remove the influences of the movement of the soil moisture and ground water from the change in gravity measured by the gravimeter. In detail, the influence of the movement of the soil moisture may be calculated by sequentially measuring a moisture content in soil using a lysimeter. However, due to a high cost for installing the lysimeter and a large volume thereof, there are many limitations on using the lysimeter. Also, the influence of the movement of ground water may be calculated by forming a ground water observation hole near the gravimeter and sequentially measuring the fluctuation in the surface of the ground water through the ground water observation hole. However, a large error occurs during a process of converting the fluctuation in the surface of the ground water into the change in gravity.

To overcome such limitations, an exemplary embodiment of the present invention provides a method of measuring a change in the density of an underground material using a gravimeter, which is capable of precisely measuring change in the density of various types of underground material by efficiently removing the influence of the movement of soil moisture and ground water using a simple method. Hereinafter, embodiments of the present invention will be described.

Figure 2:
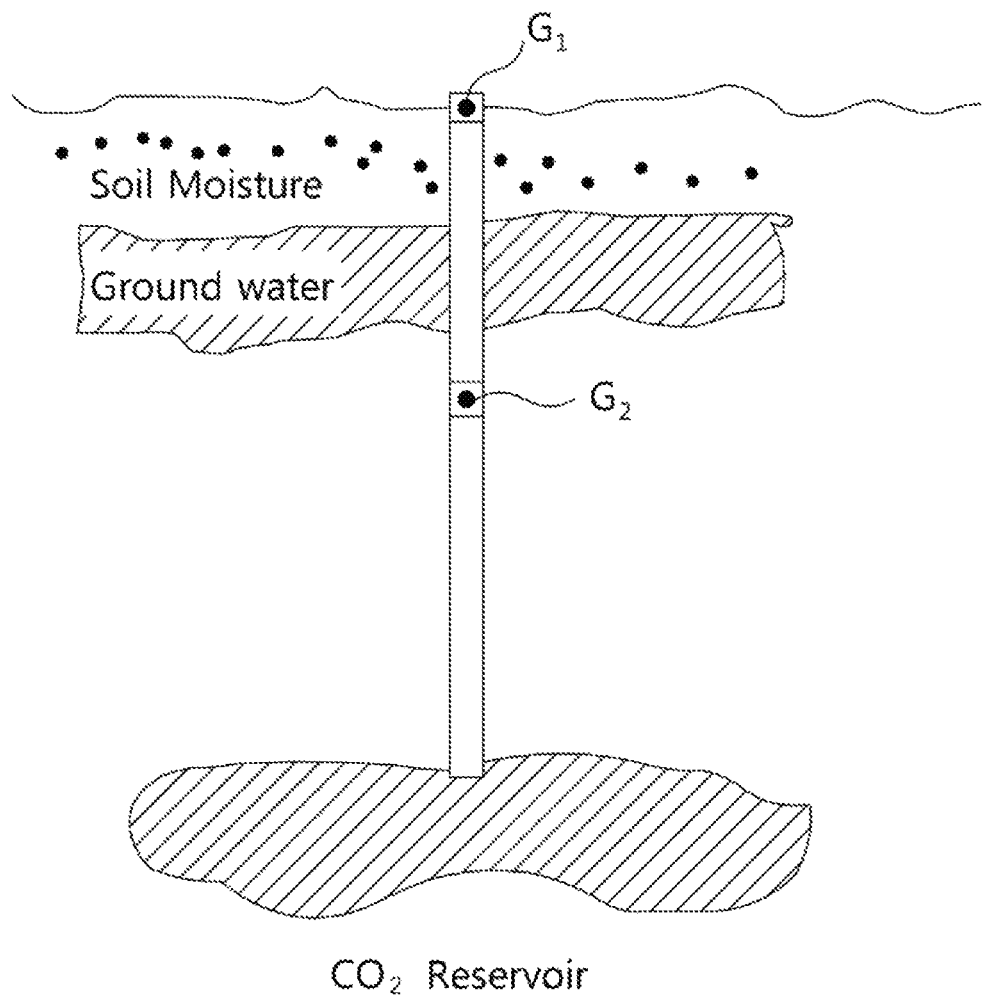
FIG. 2 is a conceptual view illustrating the method of measuring a change in the density of an underground material.

FIG. 1 is a flowchart illustrating a method of measuring a change in the density of an underground material according to an exemplary embodiment of the present invention. FIG. 2 is a conceptual view illustrating the method of measuring a change in the density of an underground material.

Referring to FIGS. 1 and 2, the method of measuring a change in the density of an underground material includes forming a borehole above a target underground material (S110), installing a first gravimeter G1 on the outside of the borehole (S120), installing a second gravimeter G2 on the inside of the borehole (S130), measuring a change in gravity using the first gravimeter G1 and the second gravimeter G2 (S140), and calculating a change in the density of the target underground material based on a first change in gravity measured by the first gravimeter G1 and a second change in gravity measured by the second gravimeter G2 (S150).

The method of measuring the change in the density of the underground material may be applied to measure a change in the density of a target underground material, such as an oil, a gas, etc., stored in an underground reservoir and carbon dioxide injected into an underground storage. Using a value of the change in density measured according to the embodiment of the present invention, it is possible to check change in the distribution of an oil, a gas, carbon dioxide, etc. which are the target underground material and the leakage thereof in real time.

To measure a change in the density of the target underground material, first, the borehole may be formed above the target underground material (S110). The borehole, for example, may be formed along a direction of the gravity of the earth from the surface to a top of a storage space of the target underground material. The borehole may be formed through a well-known method in the art and there is no limitation on a method of forming the borehole.

According to one embodiment of the present invention, during a process of forming the borehole, information about various types of earth crust material present above the target underground material may be obtained. Generally, an underground fluid which may be moved according to time, such as soil moisture, ground water, etc., is present near the surface or an underground shallow portion. The information about the various types of earth crust material may include information about content and distribution of the underground fluid which varies with a depth of the borehole.

After the borehole is formed, the first gravimeter G1 may be installed on the outside of the borehole (S120). The first gravimeter G1 may be a well-known gravimeter with no limitation and more particularly, may be a gravimeter which does not need drift correction, for example, a superconducting gravimeter. As an example, the first gravimeter G1 may be installed on the surface.

After the first gravimeter G1 is installed, the second gravimeter G2 may be installed on the inside of the borehole (S130). The second gravimeter G2 may be a well-known gravimeter with no limitation but a gravimeter which does not need drift correction, for example, a superconducting gravimeter, may be used preferably. On the other hand, the second gravimeter G2 may be a different type from the first gravimeter G1 but may be the same type as the first gravimeter G1.

An installation position of the second gravimeter G2 may be set based on information about the various types of earth crust material obtained while forming the borehole. According to one embodiment of the present invention, the second gravimeter G2 may be installed in the borehole deeper than a position at which the underground fluid such as soil moisture or ground water is present. In detail, the second gravimeter G2 may be installed at a position at which the magnitude of a first gravitational force of the underground fluid acting on the first gravimeter G1 is identical to the magnitude of a second gravitational force of the underground fluid acting on the second gravimeter G2. When the second gravimeter G2 is installed at the position inside the borehole as described above, since the first gravitational and the second gravitational forces are applied in mutually opposite directions, a gravity value measured by the first gravimeter G1 is added to a gravity value measured by the second gravimeter G2, thereby offsetting a gravitational influence caused by the underground fluid. Detailed descriptions will be described below. According to one embodiment of the present invention, 'the magnitude of the first gravitational force is identical to the magnitude of the second gravitational force' means 'an absolute difference between the first gravitational and the second gravitational forces is present within a preset error tolerance range.' For example, the error tolerance range may be set from about −10 µGal to +10 µGal.

After the first and second gravimeters G1 and G2 are installed, a change in gravity may be measured using the first gravimeter G1 and the second gravimeter G2 (S140). Hereinafter, for convenience of description, a change in gravity measured by the first gravimeter G1 is referred to as a first gravitational change and a change in gravity measured by the second gravimeter G2 is referred to as a second gravitational change.

The first gravitational change measured by the first gravimeter G1, as described above, is influenced by earth tide, ocean loading, polar motion, a change in atmospheric pressure, the movement of soil moisture and ground water, and the movement of the target underground material. Accordingly, the first gravitational change may be expressed as following Equation 1. Hereinafter, for convenience of description, among factors described above, a gravitational change caused by earth tide, a gravitational change caused by ocean loading, a gravitational change caused by polar motion, and a gravitational change caused by a change in atmospheric pressure, which may be easily calculated through actual measurement, are collectively referred to as 'a gravitational change caused by a first factor'. A gravitational change caused by the movement of soil moisture and a gravitational change caused by the movement of ground water are collectively referred to as 'a gravitational change caused by a second factor'.

$$\Delta G1 = \Delta A + \Delta B1 + \Delta T \quad \text{[Equation 1]}$$

In Equation 1, $\Delta G1$, $\Delta A$, $\Delta B1$, and $\Delta T$ indicate the first gravitational change, the gravitational change caused by the first factor, the gravitational change caused by the second factor, and the gravitational change caused by the movement of the target underground material, respectively.

The second gravitational change measured by the second gravimeter G2 is also influenced by earth tide, ocean loading, polar motion, a change in atmospheric pressure, the movement of soil moisture and ground water, and the movement of the target underground material. However, the second gravimeter G2 is influenced by earth tide, ocean loading, polar motion, a change in atmospheric pressure, and the movement of the target underground material identical to the first gravimeter G1 but is differently influenced by the movement of soil moisture and ground water from the first gravimeter G1. That is, in the second gravitational change, the gravitational change caused by the first factor has a value the same as that of the first gravitational change and the gravitational change caused by the second factor has a different value from that of the first gravitational change. Meanwhile, as described above, since the second gravimeter G2 is installed at the position at which the magnitude of the first gravitational force of the underground fluid acting on the first gravimeter G1 is identical to the magnitude of the second gravitational force of the underground fluid acting on the second gravimeter G2, the gravitational change caused by the second factor in the second gravitational change and the gravitational change caused by the second factor in the first gravitational change have the same magnitude but have mutually different acting directions. Accordingly, the second gravitational change may be expressed as following Equation 2.

$$\Delta G2 = \Delta A + \Delta B2 + \Delta T \quad \text{[Equation 2]}$$

In Equation 2, $\Delta G2$, $\Delta A$, $\Delta B2$, and $\Delta T$ indicate the first gravitational change, the gravitational change caused by the first factor, the gravitational change caused by the second factor, and the gravitational change caused by the movement of the target underground material, respectively, and $\Delta B2$ is equal to $-\Delta B1$.

Sequentially, the density of a target underground fluid may be calculated based on the first gravitational change measured by the first gravimeter G1 and the second gravitational change measured by the second gravimeter G2.

According to one embodiment of the present invention, the sum of the first gravitational change $\Delta G1$ measured by the first gravimeter G1 and the second gravitational change $\Delta G2$ measured by the second gravimeter G2 may be expressed as the following Equation 3 and the gravitational change $\Delta T$ caused by the movement of the target underground material may be expressed as the following Equation 4 from Equation 3.

$$\Delta G1 + \Delta G2 = 2\Delta A + 2\Delta T \quad \text{[Equation 3]}$$

$$\Delta T = (\Delta G1 + \Delta G2)/2 - \Delta A \quad \text{[Equation 4]}$$

Since the gravitational change $\Delta T$ caused by the movement of various types of underground material is proportional to change in the density of various types of underground material and it is possible to calculate the gravitational change $\Delta A$ caused by the first factor using a model or actual measurement, the change in the density of various types of underground material may be measured using the first gravitational change $\Delta G1$ measured by the first gravimeter G1 and the second gravitational change $\Delta G2$ measured by the second gravimeter G2.

According to exemplary embodiments of the present invention, a first gravimeter installed on the surface of the earth is vertically coupled with a second gravimeter installed in a borehole, thereby simply offsetting a change in gravity caused by the movement of soil moisture or groundwater, which is difficult to be measured or estimated. As a result, it is possible to precisely measure a change in the density of a target underground material, such as an oil, a gas, etc., stored in an underground reservoir and carbon dioxide injected into an underground storage.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A method of measuring a change in the density of an underground material over time, comprising:
   forming a borehole above a target underground material;
   installing a first gravimeter outside of the borehole and a second gravimeter inside of the borehole, wherein the first and second gravimeters are configured to measure a gravitational force caused by the target underground material;
   measuring a first gravitational change using the first gravimeter and a second gravitational change using the second gravimeter; and calculating a change in the density of the target underground material over time based on the first gravitational change and the second gravitational change.

2. The method of claim 1, wherein the target underground material is one selected from the group consisting of an underground oil, a gas, and carbon dioxide.

3. The method of claim 2, wherein the information about the earth crust material includes information about a content and distribution of an underground fluid, which varies with a depth of the borehole, and
wherein the second gravimeter is installed at a position at which a difference between an absolute value of a first gravitational force of the underground fluid acting on the first gravimeter and an absolute value of a second gravitational force of the underground fluid acting on the second gravimeter is within a preset tolerance range.

4. The method of claim 3, wherein the tolerance range is from −10 µGal to +10 µGal.

5. The method of claim 4, wherein the second gravimeter is installed above the target underground material and below the underground fluid.

6. The method of claim 3, wherein the second gravimeter is installed above the target underground material and below the underground fluid.

7. The method of claim 1, wherein information about an earth crust material existing above the target underground material is obtained in the forming of the borehole, and wherein the second gravimeter is installed at a position set based on the information about the earth crust material.

8. The method of claim 1, wherein the change in the density of the target underground material over time is calculated using a sum of the first gravitational change and the second gravitational change.

9. The method of claim 1, wherein the second gravimeter is installed above the target underground material and below an underground fluid that varies with a depth of the borehole.

* * * * *